(12) United States Patent
Wynne et al.

(10) Patent No.: US 7,060,830 B2
(45) Date of Patent: Jun. 13, 2006

(54) SYNTHESIZED γ-CARBOLINES

(75) Inventors: James H. Wynne, Alexandria, VA (US); Wayne M. Stalick, Fairfax, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 0 days.

(21) Appl. No.: 11/053,426

(22) Filed: Feb. 9, 2005

(65) Prior Publication Data

US 2005/0131010 A1    Jun. 16, 2005

Related U.S. Application Data

(63) Continuation of application No. 10/446,715, filed on May 29, 2003, now Pat. No. 6,872,830.

(60) Provisional application No. 60/448,910, filed on Feb. 24, 2003.

(51) Int. Cl.
  *C07D 471/04*   (2006.01)
  *C07D 487/04*   (2006.01)

(52) U.S. Cl. .............. 546/81; 546/79; 546/80; 546/81

(58) Field of Classification Search ............ 544/79, 544/81

See application file for complete search history.

*Primary Examiner*—Rita Desai
(74) *Attorney, Agent, or Firm*—David Yee; David G. Grossman

(57) ABSTRACT

The present invention concerns the compounds of the formula:

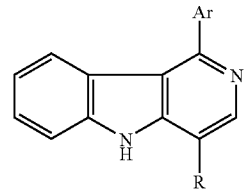

and the prodrug and salts thereof, wherein R may be a hydroxyl or other pendent group and Ar is an aryl. The compositions may be adapted for the treatment of neurodegenerative diseases. Further, the compositions may be adapted as a pharmaceutical such as an antipsychotic pharmaceutical, an antibiotic pharmaceutical, an antiviral pharmaceutical or an antitumor pharmaceutical.

3 Claims, 5 Drawing Sheets a) i) NaOEt, BrCH₂CO₂Et  ii) Bentonite K-10 Clay  iii) NaOH

SYNTHESIZED γ-CARBOLINES

CROSS-REFERENCE TO RELATED APPLICATIONS

This application is a continuation of application Ser. No. 10/446,715, filed on May 29, 2003, now U.S. Pat. No. 6,872,830 which claims the benefit of Provisional Application Ser. No. 60/448,910 to Wynne et al., filed on Feb. 24, 2003, entitled "Synthesized γ-Carbolines," the contents of which are incorporated by reference herein.

BACKGROUND OF THE INVENTION

The present invention relates to novel synthesis of γ-carbolines. More specifically, the present invention provides for synthesis of functionalized γ-carboline derivatives.

β-Carbolines, pyrido[3,4-b]indoles, are of interest to the pharmaceutical industry due to their close relationship with natural products such as tryptophan as well as their numerous reported biological activities. Through the years, a number of reports have shown that γ-carbolines, pyrido[4,3-b]indoles, also possess similar biological activities. Several substituted γ-carbolines have been synthesized and examined in a series of in vitro and in vivo pharmacological tests and have demonstrated antipsychotic, antibiotic, antitumor and other related activities.

There exists no general efficient synthetic route that allows for the formation of highly functionalized γ-carbolines, especially those that contain substituents in the 1- and 4-positions. Of the methods reported, the most widely used for γ-carboline formation is the Fischer synthesis, which often fails completely, or proceeds in low yields unless forcing thermal conditions are used or an activated pyridine ring is employed. An alternative approach is the Grabe-Ullman synthesis and subsequent modifications. This reaction involves the preparation of the phenyl-substituted triazolopyridine followed by elimination of nitrogen upon thermal degradation at temperatures ranging between 190° C. and 500° C. Microwave irradiation has also proven successful on several substrates. Likewise, the formation of a small series of γ-carbolines has been reported by the ring closure of internally generated 2-nitrosobiphenyls synthesized in situ. This reaction proceeds in moderate yields; however, the products are limited to alkyl substituted carbolines. Many of these previously reported methods requiring intramolecular cyclization, proceed in low yields, are limited to non-functional substrates, or involve extreme thermal conditions.

The formation of the desired γ-carbolines in several cases, were byproducts formed while attempting to synthesize the more notable β-carbolines. A unique three-step γ-carboline synthesis employing 4-chloropyridine and o-phenylenediamine in a catalytic palladium (II) coupling reaction was developed while two researchers, Robinson and Thornley, were attempting to synthesize β-carbolines.

Likewise, the intramolecular coupling of a boronic acid with o-fluoroiodopyridine by a Suzuki-type reaction employing a Pd (0) species has been reported. Although an efficient conversion, it involves the synthesis of specialty starting materials, and examples are few in number. The authors reported that the overall three-step process is limited to non-acid-sensitive substrates.

More recently, a novel palladium-catalyzed iminoannulation of internal alkynes was developed. This unique method allows the introduction of functionality into both the 3- and 4-positions of γ-carbolines. Additionally, Larock's group has shown that 3-substituted γ-carbolines, some of which possess 4-annularization, are readily available by a novel palladium/copper catalyzed cyclization reaction of intramolecular or terminal alkynyl indoles. These products have been compared to carbolines which act as cardiovascular agents or as 5-HT$_3$ receptor antagonists. Because of these recent advances and the importance of this class of compounds, needed is a general synthesis and novel approach to afford the complimentary series of γ-carbolines that are substituted in the 1- and 4-positions.

One possible precursor to β-carbolines is through the corresponding tetrahydro-β-carboline and subsequent derivatives. Molecules of this class have recently shown potential for multi drug resistance. The most noted method of synthesis of such proceeds via the Pictet-Spengler synthesis, which condenses triptamine, a 3-aniinomethylindole, with a variety of aldehydes. A simple method to afford the isomeric substituted tetrahydro-γ-carbolines is lacking even though these compounds are also predicted to exhibit multidrug resistance.

The lack of commercially available 3-aminomethyl indoles, or the facile synthesis of these has hindered the synthesis of the corresponding γ-carbolines. This provides an additional driving force for the development of a method to afford a large selection of functionalized γ-carbolines. A methodology is desirable which allows ease in control of substituents, especially in the 1-position and 4-position, thus creating compounds likely to exhibit desirable pharmacological and biological effects.

BRIEF SUMMARY OF THE INVENTION

One advantage of the present invention is that it provides for the generation of compounds that may easily be manipulated to achieve useful phannacologicallbiological effects.

Another advantage of this invention is that it provides for the synthesis of γ-carbolines without a need for specialty starting materials.

A further advantage of this invention is that it provides for the synthesis of tetrahydro-γ-carbolines.

Yet a further advantage of this invention is that it provides a general synthetic methodology that allows for ease in control of substituents, not only in the 1-position, but also in the 4-position.

Yet a further advantage of this invention is that it provides a general synthetic methodology that does not require extreme thermal reaction conditions.

To achieve the foregoing and other advantages, in accordance with all of the invention as embodied and broadly described herein, are compounds of the formula:

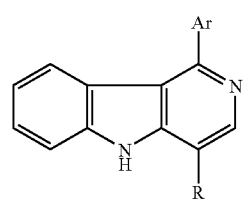

and the prodrug and salts thereof and reported precursors thereto, wherein R may be a hydroxy, alkoxy, acyl, alkyl, alkenyl, aryl group or even a hydrogen. The Ar in position 1 may be any aryl or substituted aryl group.

In yet a further aspect of the invention, are compounds of the formula:

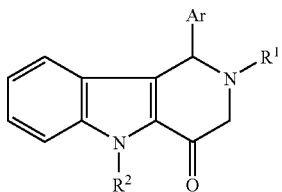

and the prodrug and salts thereof and reported precursors thereto, wherein R1 may be a tosyl, a hydrogen, or any other sulfonate group and R2 may be a hydrogen, TBDMS, or any other sterically hindered silyl group. The Ar in position 1 may be any aryl or substituted aryl group.

In yet a further aspect of the invention, these compounds may be adapted for the treatment of neurodegenerative diseases. Further, the compositions may be adapted as a pharmaceutical such as an antipsychotic pharmaceutical, an antibiotic pharmaceutical, an antiviral pharmaceutical or an antitumor pharmaceutical.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated in and form a part of the specification, illustrate embodiments of the present invention and, together with the description, serve to explain the principles of the invention.

DETAILED DESCRIPTION OF THE INVENTION

The present invention provides for synthesis of functionalized γ-carboline derivatives and their tetrahydro precursors. This synthesis also allows for the production or the facile synthesis of non-commercially available 3-aminomethyl indoles. This method may provide a large selection of functionalized γ-carbolines by controlling the substituents, not only in the 1-position, but also in the 4-position.

The following descriptions describe preferred embodiments of practicing the present invention. However, one skilled in the art will recognize that many modifications may be made to these descriptions while still obtaining the intended results.

Preferably, the present invention may start with readily available indole and proceed by a method which allows for control of substituents in the 1- and 4-positions in the final γ-carboline product, or its tetrahydro precursors.

Reagents may be obtained from commercial suppliers and may be used without further purification. Melting points may not need to be corrected; FTIR spectra of samples may be obtained in numerous ways including KBr pellets or on NaCl disks. $^1$H NMR and $^{13}$C NMR may be determined at frequencies such as 300 or 75 MHz in CDCl$_3$ or other solvents. Chemical shifts may be reported downfield from TMS. Coupling constants, J, are preferably reported in Hz. Elemental analysis may be performed using a device such as a Perkin-Elmer Series II, C, H, N-Analyzer Model 2400 or at a commercial establishment such as Atlantic Microlab, Inc. in Norcross, Ga. may be used for elemental analysis. TBF may be distilled from sodium/benzophenone ketal-pair and CH$_2$Cl$_2$ from P$_2$O$_5$, all under nitrogen. All moisture-sensitive reactions and reagent transfers may be carried out through nitrogen or argon. Thin layer chromatography ("TLC") may be performed on Eastman Kodak precoated silica gel sheets with glass backing. Preparative column chromatography may be performed on an Isco-100s automated flash column chromatograph system employing pre-packed silica gel columns 60 Å (200–400 mesh).

Figure 1:
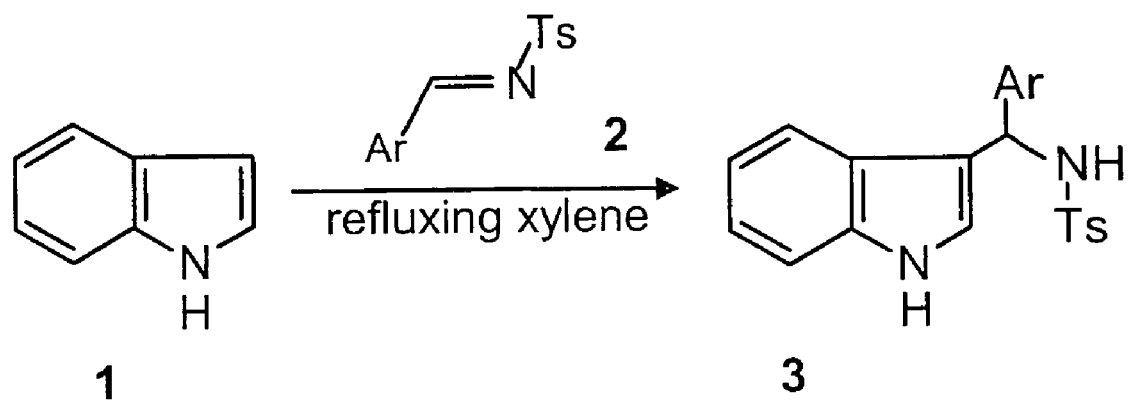
FIG. 1 shows direct treatment of indole (1) using compounds (2) in a refluxing xylene process to preferably generate substituted products (3).

Treatment of indole (1) using compound (2) in a refluxing xylene process may be used to generate substituted products (3), as shown in FIG. 1. For example, in compounds 2 and/or 3, Ar may be Ph, p-MeOPh, or p-ClPh.

The use of bulky silyl protecting groups may produce good yields when introducing various alkyl and organometallic substituents into the 3-position of the indole ring. Rearrangement, as described above, may be circumvented through the use of either a tert-butyldimethylsilyl ("TBDMS") or diisopropylsilyl ("TIPS") or other bulky silyl protecting group. The 3-bromo-1-TBDMSindole (4) may be prepared using the procedure described by Bosch and co-workers as documented in *J. Org. Chem.*, 1994, 59, 10–11.

Figure 2:
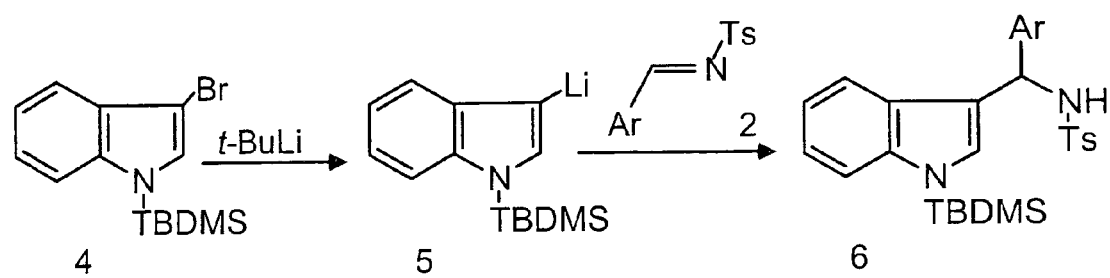
FIG. 2 shows treatment of 3-bromo-1-TBDMS indole (4) with tert-butyllithium followed by condensation with a variety of N-tosylaldimines (2), which may produce 1-protected-3-arylaminomethyl indoles (6).
Figure 3:
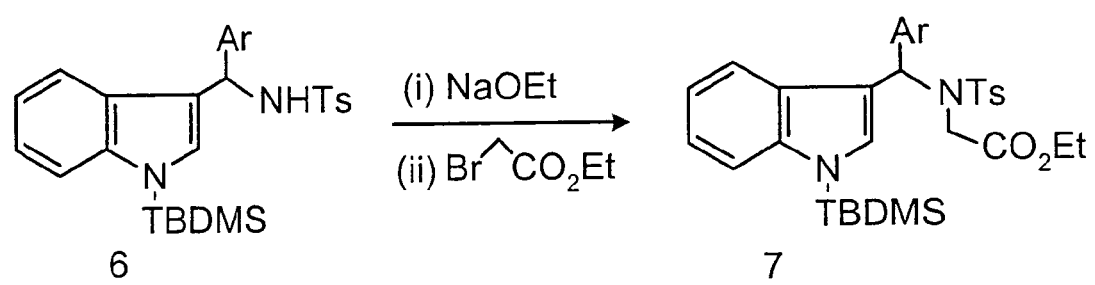
FIG. 3 shows treatment of compound (6), with sodium ethoxide followed by addition of ethyl bromoacetate, which may afford compound (7).

FIG. 2 shows treatment of 3-bromo-1-TBDMS indole (4) with tert-butyllithium followed by condensation with a variety of N-tosylaldimines (2). Other alkyl lithium reagents may also be used to afford the desired product. Such treatment may afford the corresponding 1-protected-3-arylamninomethyl indoles (6) in good yields. This procedure may allow for a wide variety of aryl substituents containing both electron withdrawing and electron donating functionalities to be introduced. The aryl substituent on tosylaldimine (2) will likely become the 1-position aryl group of the final γ-carboline molecule. Altering the tosylaldimines (2) should allow for direct control of the substituent in the 1-position of the final γ-carboline molecule.

Subsequently, treatment of 1-protected-3-arylaminomethyl indoles (6), with sodium ethoxide followed by addition of ethyl bromoacetate, may afford compound (7). A variety of bases may be employed such as sodium hydroxide, sodium hydride, potassium hydroxide, sodium methoxide, potassium methoxide or alkyl lithiums.

Figure 4:
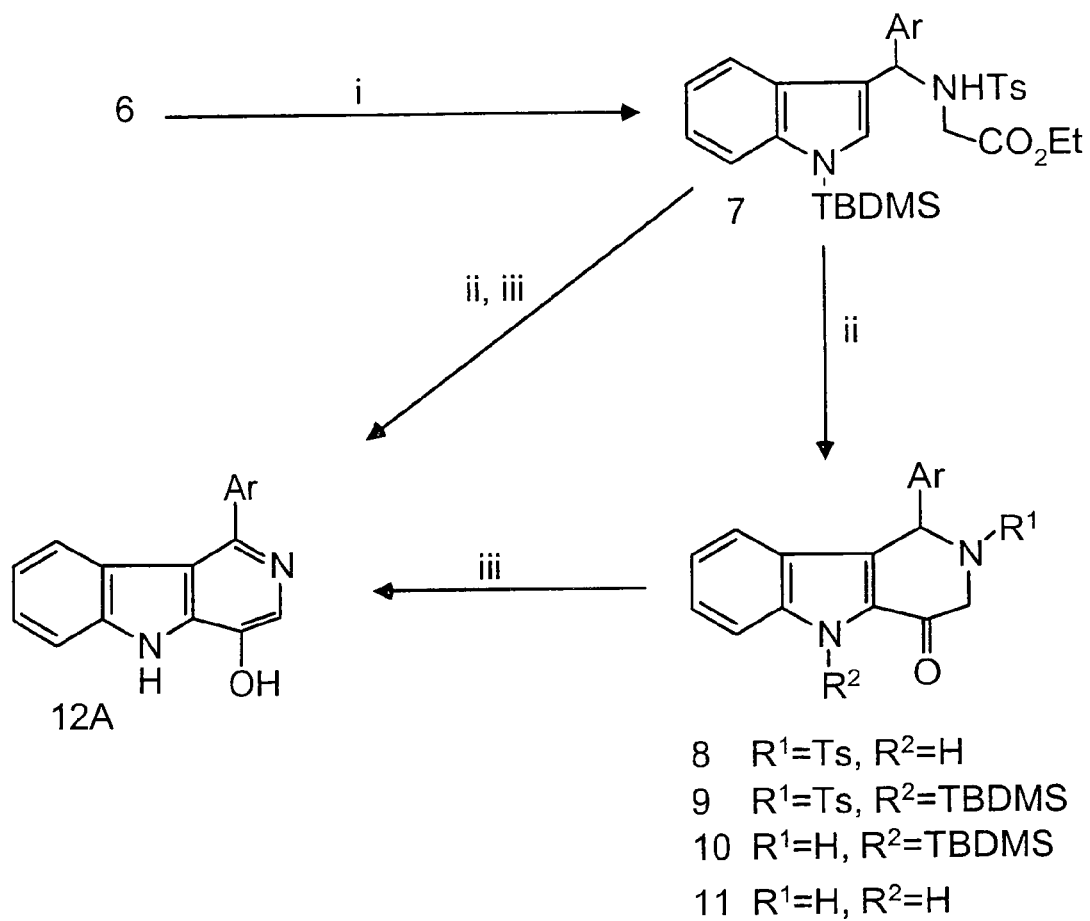
FIG. 4 shows two embodiments of creating a γ-carboline molecule as per the present invention.

FIG. 4 shows the treatment of compound (7) with a variety of Lewis acids, which may afford the desired 1,2-dihydro-3-H-γ-carbolone (8), a tetrahydro-γ-carboline, upon intramolecular cyclization. The desired carbolone (8) may afford lower yields than expected, due to contamination with compounds (9), (10) or (11). A variety of Lewis acids such as BF3*Et$_2$O, PPA, ZnCl$_2$, AlCl$_3$, TiCl$_4$, Bentonite K-10

Clay and $P_2O_5$, may be cyclizing catalysts. Bentonite K-10 Clay may yield the highest result. Stronger Lewis acids, such as $TiCl_4$, may afford a variety of products by increasing the formation of compounds (9), (10) or (11) in addition to compound (8). Since either of the compounds, (8), (9), (10) or (11), when reacted with base, may afford the desired γ-carboline (12A), it may not be necessary to isolate or purify the group of compounds that resulted from the acid catalyzed cyclization step. Direct conversion from compound (7) to (12A) may achieve good yields. When carbolone (8) is desired, scheme 4 may outline its synthesis as well.

Figure 5:
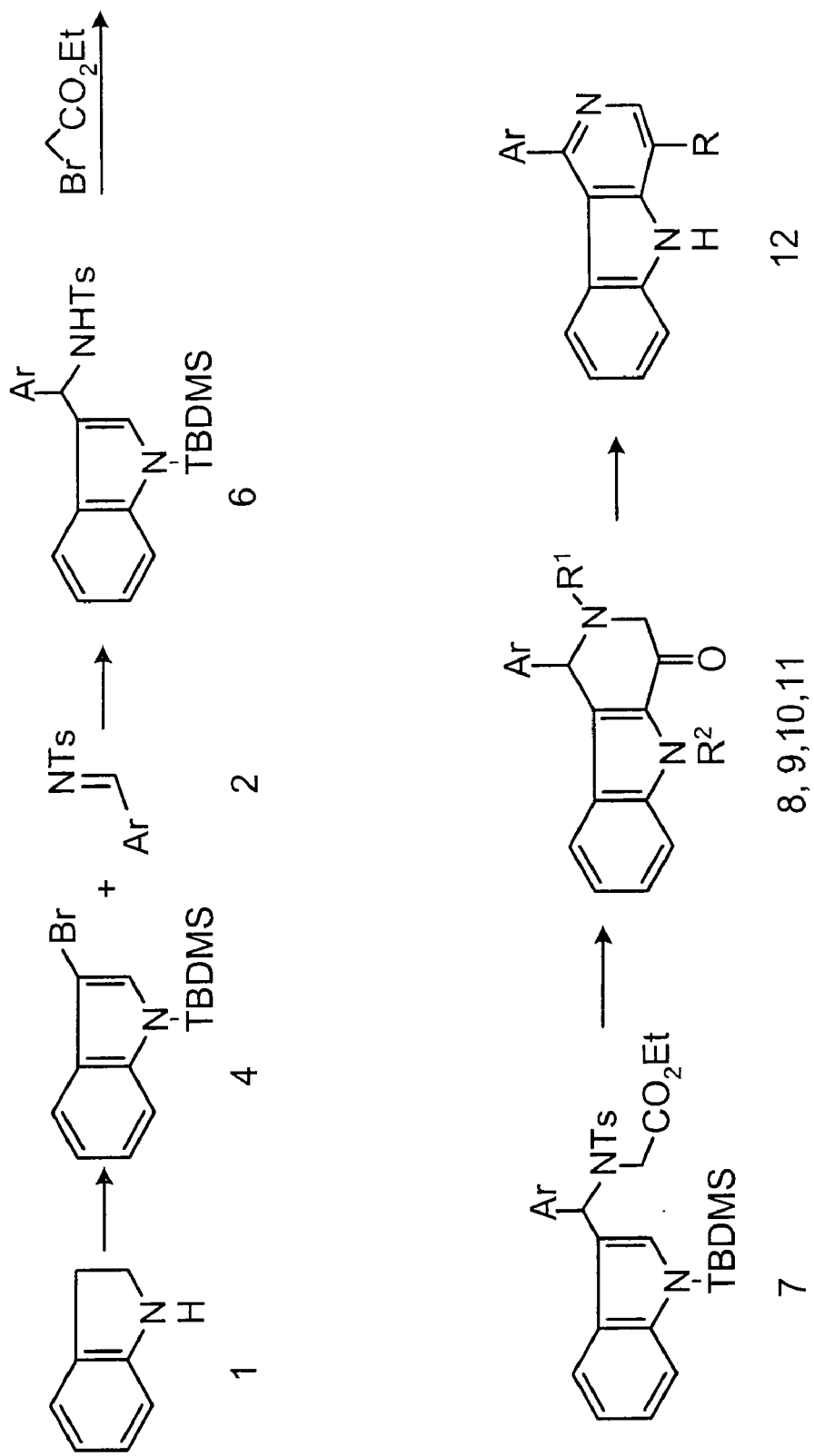
FIG. 5 shows a process of creating the present invention.

FIG. 5 shows possible intermediate steps to achieve the creation of γ-carboline products as per preferred embodiments of the present invention described herein.

The following examples and preparations are provided solely for the purpose of illustration and are not to be construed as limitations of the invention, many variations of which are possible without departing from the spirit or scope thereof.

EXAMPLE 1

Synthesis of 3-bromo-1-(tert-butyldimethylsilyl)indole (4) from indole (1)

Synthesis was performed according to a modified literature report of Bosch and co-workers as documented in *J. Org. Chem.*, 1994, 59, 10–11. To a solution of indole (4.00 g, 34.00 mmol) in 140 mL of THF at −78° C. was added dropwise a solution of n-BuLi (23.4 mL, 37.00 mmol, 1.6 M hexane solution) in a two neck half-jacketed round-bottomed flask equipped with a stir bar and a positive flow of nitrogen. The temperature was raised to −10° C. over a 15 minute period. After being stirred at −10° C. for 30 minutes, the reaction mixture was cooled to −50° C. and a solution of TBDMSCl (5.80 g, 38 mmol) in 30 mL of THF was added. After the mixture was stirred at −10° C. for 3 hours, the temperature was once again lowered to −78° C., and N-bromosuccinimide (6.00 g, 34 mmol) was added to the reaction mixture. The reaction mixture was stirred at −50° C. for 4 hours before the temperature was allowed to rise slowly to room temperature. Hexane (100 mL) and pyridine (1 mL) were added, and the resulting suspension was removed by filtration through a pad of Celite®. The filtrate was evaporated in vacuo; however, extreme caution was taken not to heat the mixture above ~65° C., at which point decomposition occurred. The crude mixture was purified by flash chromatography over silica gel using Hexane:$CH_2Cl_2$ in a 6:1 ratio affording 8.71 g (28.07 mmol) of the desired product, an 83% yield.

Preparation 1

Compounds (6a–j) from 3-bromo-1-(tert-butyldimethylsilyl)indole (4)

To a stirred solution of 3-bromo-1-(tert-butyldimethylsilyl indole (4) (0.5 g, 1.6 mmol) in THF (15 mL), cooled to −78° C., was added a-solution of t-BuLi (2.1 mL of a 1.7 M solution in pentane, 3.6 mmol). The mixture was allowed to stir for 15 minutes before the rapid addition of 1.1 equivalents of the corresponding tosylaldimine (2) (1.7 mmol) in 30 mL of THF. The solution was allowed to stir at room temperature for 12–18 hours. The reaction mixture was quenched with $H_2O$ (30 mL) and extracted with $CH_2Cl_2$ (3×15 mL). The combined organic layer was washed with $H_2O$ (2×15 mL) and dried over $MgSO_4$. The resulting organic layer was concentrated to afford a brown, viscous oil. Purification using flash column chromatography employing silica gel and a solvent system of EtOAc:Hexanes (1:4) afforded the compounds (6a–j), respectively, in approximately 50% yields.

Below illustrates the following afforded compounds (6a–j):

1. N-{[1-(tert-Butyl-dimethyl-silanyl)-1H-indol-3-yl]-phenyl-methyl}-4-methyl-benzenesulfonamide (6a): Mp=114–116° C. Elemental analysis calculated for $C_{28}H_{34}N_2O_2SSi$: C, 68.53; H, 6.98; N, 5.71. Found: C, 68.22; H, 7.11; N, 5.32.

2. N-{[1-(tert-Butyl-dimethyl-silanyl)-1H-indol-3-yl]-(4-methoxy-phenyl)-methyl}-4-methyl-benzenesulfonamide (6b): Mp=155–156° C. Elemental analysis calculated for $C_{29}H_{36}N_2O_3SSi$: C, 66.89; H, 6.97; N, 5.38. Found: C, 66.54; H, 6.67; N, 5.01.

3. N-{[1-(tert-Butyl-dimethyl-silanyl)-1H-indol-3-yl]-(4-chloro-phenyl)-methyl}-4-methyl-benzenesulfonamide (6c): Mp=135–137° C. Elemental analysis calculated for $C_{28}H_{33}ClN_2O_2SSi$: C, 64.04; H, 6.33; N, 5.33. Found: C, 63.81; H, 6.13; N, 5.71.

4. N-{[1-(tert-Butyl-dimethyl-silanyl)-1H-indol-3-yl]-pyridin-2-yl-methyl}-4-methyl-benzenesulfonamide (6d): Oil. Elemental analysis calculated for $C_{27}H_{33}N_3O_2SSi$: C, 65.95; H, 6.76; N, 8.55. Found: C, 65.63; H, 6.92; N, 8.81.

5. N-{[1-(tert-Butyl-dimethyl-silanyl)-1H-indol-3-yl]-(2-trifluoromethyl-phenyl)-methyl}-4-methyl-benzenesulfonamide (6e): Mp=199–202° C. Elemental analysis calculated for $C_{29}H_{33}F_3N_2O_2SSi$: C, 62.34; H, 5.95; N, 5.01. Found: C, 62.74; H, 6.12; N, 4.78.

6. N-{[1-(tert-Butyl-dimethyl-silanyl)-1H-indol-3-yl]-thiophen-2-yl-methyl}-4-methyl-benzenesulfonamide (6f): Mp=152–154° C. Elemental analysis calculated for $C_{26}H_{32}N_2O_2S_2Si$: C, 62.86; H, 6.49; N, 5.64. Found: C, 62.97; H, 6.21; N, 5.83.

7. N-{Anthracen-9-yl-[1-(tert-butyl-dimethyl-silanyl)-1H-indol-3-yl]-methyl}-4-methyl-benzenesulfonamide (6g): Mp=158–161° C. Elemental analysis calculated for $C_{36}H_{38}N_2O_2SSi$: C, 73.18; H, 6.48; N, 4.74. Found: C, 72.89; H, 6.47; N, 4.53.

8. N-{[1-(tert-Butyl-dimethyl-silanyl)-1H-indol-3-yl]-(2-nitro-phenyl)-methyl}-4-methyl-benzenesulfonamide (6h): Mp=219–220° C. Elemental analysis calculated for $C_{28}H_{33}N_3O_4SSi$: C, 62.77; H, 6.21; N, 7.84. Found: C, 62.54; H, 5.87; N, 8.02.

9. N-{[1-(tert-Butyl-dimethyl-silanyl)-1H-indol-3-yl]-furan-2-yl-methyl}-4-methyl-benzenesulfonamide (6i): Semi-solid. Elemental analysis calculated for $C_{26}H_{32}N_2O_3SSi$: C, 64.96; H, 6.71; N, 5.83. Found: C, 65.21; H, 6.58; N, 5.78.

10. N{N[1-(tert-Butyl-dimethyl-silanyl)-1H-indol-3-yl]-quinolin-2-yl-methyl}-4-methyl-benzenesulfonamide (6j): Oil. Elemental analysis calculated for $C_{31}H_{35}N_3O_2SSi$: C, 68.72; H, 6.51; N, 7.76. Found: C, 69.03; H, 6.57; N, 7.94.

Preparation 2

Synthesis of Compounds (7a–g) from Compound 6

In a 50 mL round bottom flask was placed a sample of compound (6) (2.01 mmol) dissolved in 30 mL of THF. This mixture was allowed to stir under a positive flow of $N_2$ for 15 minutes. Sodium ethoxide (2.21 mmol) was added to the stirred solution and stirring was continued for an additional 30 minutes before adding ethyl bromoacetate (2.52 mmol). The resulting solution was heated at reflux for 3.5 hours and allowed to cool slowly to room temperature before quenching with 10 mL of $H_2O$. The resulting solution was extracted with $CH_2Cl_2$ (3×25 mL), washed with $H_2O$ (3×15 mL) and dried over $MgSO_4$ before concentrating. The final traces of solvent were removed under vacuum for 12 hours. Gradient flash column chromatography (hexane:ethyl acetate) was performed to afford the product.

The following compounds illustrate the various products generated from this procedure:

1. [[[1-TBDMS-1H-indol-3-yl]-phenyl-methyl]-(toluene-4-sulfonyl)-amino]-acetic acid ethyl ester (7a): A viscous red oil, 86% yield. Elemental analysis calculated for $C_{32}H_{40}N_2O_4SSi$: C, 66.63; H, 6.99; N, 4.86. Found: C, 66.28; H, 7.14; N, 4.61.
2. [[[1-TBDMS-1H-indol-3-yl]-(4-methoxy-phenyl)-methyl]-(toluene-4-sulfonyl)-amino]-acetic acid ethyl ester (7b): A yellow powder, 72% yield. Mp=110–112.5° C. Elemental analysis calculated for $C_{33}H_{42}N_2O_5SSi$: C, 65.31; H, 6.98; N, 4.62. Found: C, 65.67; H, 7.03; N, 4.34.
3. [[[1-TBDMS-1H-indol-3-yl]-(4-chloro-phenyl)-methyl]-(toluene-4-sulfonyl)-amino]-acetic acid ethyl ester (7c): A yellow oil, 63% yield. Elemental analysis calculated for $C_{32}H_{39}ClN_2O_4SSi$: C, 62.88; H, 6.43; N, 4.58. Found: C, 62.55; H, 6.22; N, 4.88.
4. [[[1-TBDMS-1H-indol-3-yl]-pyridin-2-yl-methyl]-(toluene-4-sulfonyl)-amino]-acetic acid ethyl ester (7d): A yellow powder, 61% yield. Mp=87.5–93° C. Elemental analysis calculated for $C_{31}H_{39}N_3O_4SSi$: C, 64.44; H, 6.80; N, 7.27. Found: C, 64.13; H, 7.12; N, 6.93.
5. [[[1-TBDMS-1H-indol-3-yl]-(2-trifluoromethyl-phenyl)-methyl]-(toluene-4-sulfonyl)-amino]-acetic acid ethyl ester (7e): A yellow oil, 59% yield. Elemental analysis calculated for $C_{33}H_{39}F_3N_2O_4SSi$: C, 61.47; H, 6.10; N, 4.34. Found: C, 61.14; H, 5.86; N, 3.97.
6. [[[1-TBDMS-1H-indol-3-yl]-thiophen-2-yl-methyl]-(toluene-4-sulfonyl)-amino]-acetic acid ethyl ester (7f): A brown powder, 43% yield. Mp=87.5–93° C. Elemental analysis calculated for $C_{30}H_{38}N_2O_4S_2Si$: C, 61.82; H, 6.57; N, 4.81. Found: C, 61.71; H, 6.32; N, 5.18.
7. [[Anthracen-9-yl-[1-TBDMS-1H-indol-3-yl]-methyl]-(toluene-4-sulfonyl)-amino]-acetic acid ethyl ester (7g): A yellow oil, 61% yield. Elemental analysis calculated for $C_{40}H_{44}N_2O_4SSi$: C, 70.97; H, 6.55; N, 4.14. Found: C, 71.36; H, 6.46; N, 3.83.

Preparation 3

Synthesis of Compound (8) from Compound (7)

Into a 50 mL round bottom flask a sample of compound (7) (8.42 mmol) was dissolved in 25 mL of THF. The solution was allowed to stir under a positive flow of $N_2$ for 15 minutes. To the stirred solution was added 1.00 g of Bentonite K-10 clay. The resulting solution was heated in an 80° C. oil bath for 12 hours. Upon completion, the reaction mixture was cooled, then diluted with 20 mL $CH_2Cl_2$ and vacuum filtered with the aid of a Büchner funnel to remove the clay from the reaction mixture. The organic layer was dried over $MgSO_4$ and concentrated under reduced pressure. Final traces of solvent were removed under vacuum 4 hr. Gradient flash column chromatography (hexane:ethyl acetate) was performed to afford the desired product (8).

The following compounds illustrate the various solutions from this preparation:

1. 1-Phenyl-2-(toluene-4-sulfonyl)-1,2,3,5-tetrahydro-pyrido[4,3-b]indol-4-one (8a): 61%. Elemental analysis calculated for $C_{24}H_{20}N_2O_3S$: C, 69.21; H, 4.84; N. 6.73. Found: C, 68.97; H, 5.13; N, 6.49.
2. 1-(4-Methoxy-phenyl)-2-(toluene-4-sulfonyl)-1,2,3,5-tetrahydro-pyrido[4,3-b]indol-4-one (8b): Dark oil, 45% yield (6 mg, 0.01 mmol). Elemental analysis calculated for $C_{25}H_{22}N_2O_4S$: C, 67.25; H, 4.97; N, 6.27. Found: C, 67.04; H, 5.16; N, 6.19.
3. 1-(4-Chloro-phenyl)-2-(toluene-4-sulfonyl)-1,2,3,5-tetrahydro-pyrido[4,3-b]indol-4-one (8c): 57%. Elemental analysis calculated for $C_{24}H_{19}ClN_2O_3S$: C, 63.92; H, 4.25; N, 6.21. Found: C, 64.01; H, 4.52; N, 5.93.

Preparation 4

Synthesis of Compound (11) from Compound (7)

Into a 50 mL round bottom flask a sample of compound (7) (8.42 mmol) was dissolved in 25 mL of THF. The solution was allowed to stir under a positive flow of $N_2$ for 15 minutes. To the stirred solution was added 1.00 g of Bentonite K-10 clay. The resulting solution was heated in an 80° C. oil bath for 12 hours. The reaction was cooled, vacuum filtered with the aid of a Büchner funnel to remove the clay from the reaction mixture. To the resulting combined organic layer was added 20 mL THF, NaOH (16.84 mmol) and tetrabutylammonium bromide (0.84 mmol). The solution was heated at reflux for 6 hours, allowed to slowly cool to room temperature, diluted with 20 mL $CH_2Cl_2$ and neutralized with 1M HCl. The resulting solution was washed with $H_2O$ (3×20 mL) and Brine (1×15 mL). The organic layer was dried over $MgSO_4$ and concentrated under reduced pressure. Final traces of solvent were removed under vacuum for 4 hours. Gradient flash column chromatography (hexane:ethyl acetate) was performed to afford the desired product (11).

The following compounds illustrate the various products generated from this procedure:

1. 1-Phenyl-5H-pyrido[4,3-b]indol-4-ol (11a): A yellow oil, 35% yield (from compound (7)). Elemental analysis calculated for $C_{17}H_{12}N_2O$: C, 78.44; H, 4.65; N, 10.76. Found: C, 78.21; H, 4.58; N; 10.43.
2. 1-(4-Methoxy-phenyl)-5H-pyrido[4,3-b]indol-4-ol (11b): A yellow oil, 31% yield (from compound (7)). Elemental analysis calculated for $C_{18}H_{14}N_2O_2$: C, 74.47; H, 4.86; N, 9.65. Found: C, 74.09; H, 4.75; N, 9.51.
3. 1-(4-Chloro-phenyl)-5H-pyrido[4,3-b]indol-4-ol (11c): A yellow oil, 28% yield (from compound (7)). Elemental analysis calculated for $C_{17}H_{11}ClN_2O$: C, 69.28; H, 3.76; N, 9.50. Found: C, 68.93; H, 3.54; N, 9.79.
4. 1-Pyridin-2-yl-5H-pyrido[4,3-b]indol-4-ol (11d): A brown oil, 33% yield (from compound (7)). Elemental analysis calculated for $C_{16}H_{11}N_3O$: C, 73.55; H, 4.24; N, 16.08. Found: C, 73.39; H, 4.08; N, 15.99.
5. 1-(2-Trifluoromethyl-phenyl)-5H-pyrido[4,3-b]indol-4-ol (11e): A yellow oil, 43% yield (from compound (7)). Elemental analysis calculated for $Cl_{18}H_{11}F_3N_2O$: C, 65.85; H, 3.38; N, 8.53. Found: C, 66.02; H, 3.57; N, 8.46.
6. 1-Thiophen-2-yl-5H-pyrido[4,3-b]indol-4-ol (11f): A yellow oil, 18% yield (from compound (7)). Elemental analysis calculated for $C_{15}H_{10}N_2OS$: C, 67.65; H, 3.78; N, 10.52. Found: C, 67.78; H, 3.69; N, 10.35.
7. 1-Anthracen-9-yl-5H-pyrido[4,3-b]indol-4-ol (11g): An orange oil, 26% yield (from compound (7)). Elemental analysis calculated for $C_{25}H_{16}N_2O$: C, 83.31; H, 4.47; N, 7.77. Found: C, 83.58; H. 4.63; N, 8.06.

Preparation 5

Synthesis of Compound (12) from Compound (8)

Compound (8) was dissolved in 25 mL of THF and allowed to stir for 15 minutes before the addition of NaOH (16.84 mmol) and tetrabutylammonium bromide (0.84 mmol). The resulting solution was heated at reflux for 6 hours and then allowed to slowly cool to room temperature, diluted with 20 mL $CH_2Cl_2$ and neutralized with 1M HCl. The resulting solution was washed with $H_2O$ (3×20 mL) and brine (1×15 mL). The organic layer was dried over $MgSO_4$ and concentrated under reduced pressure. Final traces of solvent may be removed under vacuum for 4 hours. Gradient flash column chromatography (hexane:ethyl acetate) may be performed to afford the desired product (11).

The foregoing descriptions of the preferred embodiments of the present invention have been presented for purposes of illustration and description. They are not intended to be exhaustive or to limit the invention to the precise forms disclosed, and obviously many modifications and variations are possible in light of the above teaching. For example, THF could be substituted with other organic solvents such as ethers, esters, or amides. The illustrated embodiments were chosen and described in order to best explain the principles of the invention and its practical application to thereby enable others skilled in the art to best utilize the invention in various embodiments and with various modifications as are suited to the particular use contemplated. Any reference to claim elements in the singular, e.g. using the articles "a," "an," "the," or "said" is not construed as limiting the element to the singular.

What is claimed is:

1. A compound according to formula:

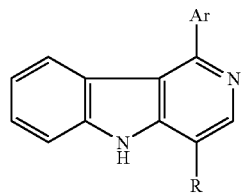

or a salt thereof, wherein R is a substituent selected from group consisting of a hydrogen, or a hydroxyl, and wherein Ar is a group selected from pyridine or thiophene.

2. A compound according to claim 1, which is 1-Pyridin-2-yl-5H-pyrido[4,3-b]indol-4-ol.

3. A compound according to claim 1, which 1-Thiophen-2-yl-5H-pyrido[4,3-b]indol-4-ol.

* * * * *